United States Patent [19]
Peterson et al.

[11] Patent Number: 5,972,608
[45] Date of Patent: Oct. 26, 1999

[54] ASSAYS AND REAGENTS FOR CHROMATIN REMODELING ENZYMES AND THEIR MODULATORS

[75] Inventors: Craig L. Peterson; Colin Logie, both of Worcester, Mass.

[73] Assignee: University of Massachusetts, Boston, Mass.

[21] Appl. No.: 08/920,165

[22] Filed: Aug. 27, 1997

[51] Int. Cl.$^6$ .............................. C12Q 1/68; C07H 21/04; C07K 13/00; G01N 33/53
[52] U.S. Cl. ................................. 435/6; 435/5; 435/91.1; 536/22.1; 536/23.1; 536/24.3; 536/24.31; 536/24.33; 530/300; 530/350; 436/501; 436/518
[58] Field of Search ................................... 435/5, 6, 91.1; 536/22.1, 23.1, 24.3, 24.31, 24.33, 24.5; 530/300, 350; 436/501, 518

[56] References Cited

PUBLICATIONS

O'Neill et al, "Nucleosome arrays inhibit both initiation and elongation of transcripts by bacteriophage T7 RNA polymerase", J. Mol. Biol. 223(1):67–78, 1992.

Cote et al., "Stimulation of GAL4 Derivative Binding to Nucleosomal DNA by the Yeast SWI/SNF Complex", Science, vol. 265, pp. 53–60, Jul. 1, 1994.

Hansen et al., "Large–Scale Purification of Plasmid Insert DNA Sequences Using Low–Percentage Agarose Exclusion Chromatography", Analytical Biochemistry, vol. 179, pp. 167–170, May, 15, 1989.

Hansen et al., "Assembly and Structural Properties of Subsaturated Chromatin Arrays", The Journal of Biological Chemistry, vol. 268, pp. 5840–5848, Mar. 15, 1993.

Hansen et al., "Homogeneous Reconstituted Oligonucleosomes, Evidence for Salt–Dependent Folding in the Absence of Histone H1", Biochemistry, vol. 28, pp. 9129–9136, 1989.

Imbalzano et al., "Nucleosome Disruption by Human SWI/SNF Is Maintained in the Absence of Continued ATP Hydrolysis", The Journal of Biological Chemistry, vol. 271, pp. 20726–20733, Aug. 23, 1996.

Imbalzano et al., "Facilitated Binding of TATA–Binding Protein to Nucleosomal DNA", Nature, vol. 370, pp. 481–485, Aug. 11, 1994.

Kwon et al., Nucleosome Disruption and Enhancement of Activator Binding by a Human SW1/SNF Complex, Nature, vol. 370, pp. 477–481, Aug. 11, 1994.

Owen–Hughes et al., Persistent Site–Specific Remodeling of a Nucleosome Array by Transient Action of the SWI/SNF Complex, Science, vol. 273, pp. 513–516, Jul. 26, 1996.

Owen–Hughes et al., Remodeling the Chromatin Structure of a Nucleosome Array by Transcription Factor–Targeted Trans–Displacement of Histones, The Embo Journal, vol. 15, pp. 4702–4712, 1996.

Polach et al., "Mechanism of Protein Access to Specific DNA Sequences in Chromatin: A Dynamic Equilibrium Model for Gene Regulation", J. Mol. Biol. vol. 254, pp. 130–149, 1995.

Quinn et al., "DNA–Binding Properties of the Yeast SWI/SNF Complex", Nature, vol. 379, pp. 844–847, Feb. 29, 1996.

Schwartz et al., "Formation and Stability of Higher Order Chromatin Structures", The Journal of Biological Chemistry, vol. 269, pp. 16284–16289, Jun. 10, 1994.

Simpson et al., "Chromatin Reconstituted from Tandemly Repeated Cloned DNA Fragments and Core Histones: A Model System for Study of Higher Order Structure", Cell, vol. 42, pp. 799–808, Oct. 1985.

Tsukiyama et al., "Purification and Properties of an ATP–Dependent Nucleosome Remodeling Factor", Cell, vol. 83, pp. 1101–1120, Dec. 15, 1995.

Tsukiyama et al., "ATP–Dependent Nucleosome Disruption at a Heat–Shock Promoter Mediated by Binding of GAGA Transcription Factor", Nature, vol. 367, pp. 525–532, Feb. 10, 1994.

Utley et al., "SWI/SNF Stimulates the Formation of Disparate Activator–Nucleosome Complexes but is Partially Redundant with Cooperative Binding", The Journal of Biological Chem., vol. 272, pp. 12642–12649, May 9, 1997.

Primary Examiner—Jeffrey Fredman
Attorney, Agent, or Firm—Fish & Richardson P.C.

[57] ABSTRACT

Disclosed are new nucleosome arrays that can be used in assays that couple the activity of a chromatin remodeling enzyme (or enzyme complex) to the activity of a restriction endonuclease to quantitatively measure the extent of "remodeling" activity exhibited by a particular remodeling enzyme or enzyme complex. Further, the new nucleosome arrays can be used in methods for screening candidate modulators, i.e., inhibitors or enhancers, of chromatin remodeling enzymes or enzyme complexes.

17 Claims, 7 Drawing Sheets

ASSAYS AND REAGENTS FOR CHROMATIN REMODELING ENZYMES AND THEIR MODULATORS

STATEMENT AS TO FEDERALLY SPONSORED RESEARCH

This invention was made with Government support under grant number GM49650-04 awarded by NIH. The Government may have certain rights in the invention.

BACKGROUND OF THE INVENTION

The invention relates to simple assay systems for monitoring and measuring the activity of chromatin remodeling enzymes and modulators of these enzymes.

Chromatin remodeling enzymes and enzyme complexes are composed of at least one polypeptide and interact with nucleosomes to either stabilize or destabilize the nucleosome structure. The action of a chromatin remodeling enzyme leads to the enhanced or decreased accessibility of nucleosomal DNA sequences and thus affects nuclear processes that utilize DNA as a substrate, e.g., transcription, replication, DNA repair, and DNA organization within the nucleus, as well as the regulators of these processes.

Examples of chromatin remodeling enzymes and enzyme complexes include the yeast SWI/SNF complex and its homologues, which have been found in mice, humans, and flies and are likely present in all or most eukaryotes. To date, besides the SWI/SNF complex, four other complexes have been described that display the capacity to remodel nucleosomes in an ATP-dependent fashion. These complexes are: the NUcleosome Remodeling Factor complex ("NURF," Tsukiyama, T. and Wu, C., Cell, 83:1011–1020, 1995); the CHRomatin Accessibility Complex ("CHRAC," Varga-Weisz et al., EMBO J., 14:2209–2216, 1995); the ATP utilizing Chromatin assembly and remodeling Factor complex ("ACF," Ito et al., Cell, 90:145–155, 1997); and the Remodels the Structure of Chromatin complex ("RSC," Cairns et al., Cell, 87:1249–1260, 1996). The former three have been found in *Drosophila melanogaster* and the latter in *Saccharomyces cerevisiae*. Besides these five known macromolecular nucleosome remodeling complexes, there are numerous other nuclear enzymes (and enzyme complexes) that have the capacity to covalently modify the histone components of the nucleosomes.

It also has been suggested that covalent modification of histones (e.g., acetylation, phosphorylation, methylation, and ubiquitination) can by itself result in chromatin remodeling, and that such histone modifications can affect the activity of the above ATP-dependent molecular nucleosome remodeling complexes. The study of these remodeling enzymes has become increasingly important as a way to analyze chromatin structure and its site-specific remodeling in the regulation of gene expression. Thus, the characterization of these enzymes or enzyme complexes, which appear to interact directly with nucleosomes to stabilize or destabilize nucleosome structure and thereby repress or activate gene expression, and their modulators, is necessary to understand basic transcriptional regulatory mechanisms such as the regulation of gene expression during developmental processes.

Chromatin, the structure into which DNA in eukaryotes is neatly packaged, contains DNA, RNA, and protein in a compact form in which the majority of DNA sequences are structurally inaccessible and functionally inactive. Within this mass of sequences are a minority of active sequences, access to which is also structurally inhibited. Chromatin, in its simplest state, the nucleosome core particle ("nucleosome"), consists of about 146 base pairs of DNA wrapped around a histone core, i.e., an octamer of two of each of four different histone proteins (H2A, H2B, H3, and H4). This nucleoprotein structure presents a natural barrier to the process of RNA transcription, inhibiting both the accessibility of the general transcription machinery to promoter sequences and the binding of upstream regulatory proteins. The nucleoprotein structure also presents a barrier to DNA binding proteins involved in other types of nuclear processes. As their name suggests, chromatin remodeling enzymes function to facilitate transcription by remodeling chromatin, i.e., by providing access to DNA that would otherwise remain inaccessible.

The prototype and best characterized of the nucleosome remodeling enzyme complexes is the yeast (*S. cerevisiae*) SWI/SNF complex, which consists of 11 tightly associated subunits. Treich et al., *Mol. Cell. Biol.*, 15:4240–4248 (1995). Genetic studies in *S. cerevisiae* indicate that the SWI/SNF complex is required for the induction of a class of genes regulated at the transcriptional level and that it functions by antagonizing chromatin-mediated transcriptional repression. Burns, L. G. and Peterson, C. L., *Biochim. Biophys. Acta*, 1350:159–68 (1997).

Previous in vitro studies have established that the yeast SWI/SNF complex destabilizes nucleosomes in vitro and that ATP hydrolysis is required for this reaction to occur. Cote et al., *Science*, 265:53–60 (1994). Furthermore, while the SWI/SNF remodeling reaction involves a disruption of DNA-histone interactions, it does not by itself result in nucleosome displacement. Cote et al., *Science*, 265:53–60 (1994); Owen-Hughes et al., *Science*, 273:513–516 (1996). SWI/SNF activity can also lead to an enhanced affinity of transcription factors for their binding sites when these sites are incorporated into nucleosomes. Cote et al., *Science*, 265:53–60 (1994); Owen-Hughes et al., *Science*, 273:513–6 (1996); Utley et al., *J. Biol. Chem.*, 272:12642–12649 (1997). Previous studies have also shown that the yeast SWI/SNF complex displays nanomolar affinity for DNA fragments longer than 200 base pairs and for synthetic four-way DNA junctions, moreover, ATPase activity is stimulated by these DNAs. Quinn et al., *Nature*, 379:844–847 (1996).

SUMMARY OF THE INVENTION

The invention features new nucleosome arrays that can be used in assays that couple the activity of a chromatin remodeling enzyme (or enzyme complex) to the activity of a restriction endonuclease to quantitatively measure the extent of "remodeling" activity exhibited by a particular remodeling enzyme or enzyme complex. Further, the new nucleosome arrays can be used in arrays that measure the extent of activity exhibited by a particular modulator, i.e., an activator or inhibitor, of a specific chromatin remodeling enzyme or enzyme complex. In particular, the invention features a two enzyme, coupled reaction wherein nucleosomal DNA in an array of multiple nucleosomes must first be disrupted by a chromatin remodeling enzyme to serve as an efficient substrate for digestion with a restriction endonuclease. The rate of cleavage exhibited by the restriction enzyme, which is indicative of the accessibility of the nucleosomal DNA, is then determined as measured against a standard rate of cleavage to allow direct comparisons of accessibility resulting from the activity of the chromatin remodeling enzymes or enzyme complexes and/or modulators of these enzymes or enzyme complexes.

In general, the invention features a nucleosome array including (a) a plurality, e.g., at least 6, of DNA sequence repeats of, for example, each from about 146 base pairs to about 240 base pairs in length, e.g., 208 base pairs, linked to form a linear chain of DNA repeats wherein each DNA sequence in the linear chain is a nucleosome positioning sequence; and (b) a number of histone octamer cores equal to the number of DNA repeats, wherein each of the histone octamer cores is associated with one of the DNA sequence repeats to form a nucleosome, wherein at least one of the DNA sequence repeats comprises a unique endonuclease restriction site.

In this nucleosome array, the DNA sequence repeats can be derived from, i.e., include a portion of, the 5S rRNA gene from L. variegatus, and the 5S rRNA gene from X. Borealis, and one or two, or more, of DNA sequence repeats can include a single, unique endonuclease restriction site. In addition, the DNA sequence repeat or repeats including the single, unique endonuclease restriction site can be positioned between two of the other DNA sequence repeats of the linear chain.

In another embodiment, the invention features a method for quantitatively measuring the accessibility of nucleosomal DNA. The method includes the steps of (a) obtaining a nucleosome array including a plurality of DNA sequence repeats, at least one of the DNA sequence repeats comprising a unique endonuclease restriction site; (b) incubating the nucleosome array with a chromatin remodeling enzyme to generate a substrate for digestion with the restriction endonuclease; (c) digesting the substrate with the restriction endonuclease; and (d) comparing the rate of restriction endonuclease cleavage of the substrate with a standard level of cleavage; whereby the comparative rate of cleavage is indicative of the accessibility of the nucleosomal DNA.

In this method, the DNA sequence repeats can be linked to form a linear chain of DNA repeats, each DNA sequence in the linear chain can be a nucleosome positioning sequence, and the nucleosome array can further include a number of histone octamer cores equal to the number of DNA repeats, wherein each of the histone octamer cores is associated with one of the DNA sequence repeats to form a nucleosome. In addition, the chromatin remodeling enzyme can be the SWI/SNF complex, a homologue of the SWI/SNF complex, NURF, CHRAC, ACF, RSC, or a histone post-translational modifying enzyme.

In another aspect, the invention also features a method for identifying a candidate compound as a modulator, e.g., inhibitor or enhancer, of a chromatin remodeling enzyme. This method includes the steps of (a) obtaining a nucleosome array including a plurality of DNA sequence repeats, at least one of the DNA sequence repeats comprising a unique endonuclease restriction site, e.g., as described herein; (b) incubating the nucleosome array with a chromatin remodeling enzyme and the candidate compound to generate a substrate for digestion with the restriction endonuclease; (c) digesting the substrate with the restriction endonuclease; and (d) comparing the level of restriction endonuclease cleavage of the substrate with a standard level of cleavage; whereby an increase or decrease in the level of cleavage indicates the candidate compound is a modulator of the chromatin remodeling enzyme. In this method, the chromatin remodeling enzyme can be the SWI/SNF complex, a homologue of the SWI/SNF complex, NURF, CHRAC, ACF, RSC, or a histone post-translational modifying enzyme.

The invention further features compounds identified by the methods described herein.

A "chromatin remodeling enzyme" or "chromatin remodeling enzyme complex" is an enzyme or enzyme complex that can stabilize or destabilize the structure of chromatin, e.g., a nucleosome.

A "nucleosome positioning sequence" is a DNA sequence that preferentially and repeatably associates with a histone octamer core along its length to form a nucleosome in which the same portion of the DNA sequence is positioned at the dyad axis of the nucleosome. A DNA sequence that is "associated with" a histone core is wrapped or coiled around the core and maintained in a normally stable relationship with the core, e.g., by electrostatic forces.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The assays described herein are simple, rapid, easily quantitated, and utilize a substrate, the new nucleosome arrays, that resemble or mimic physiological chromatin. These assays are particularly useful in high throughput screens for identifying compounds, e.g., in combinatorial libraries (such as chemical or small molecule libraries), that can modulate chromatin remodeling reactions in vito and thus also in vivo.

The assays can also be used to probe DNA accessibility in the context of the new nucleosome arrays, and thus determine the kinetic properties of chromatin remodeling enzymes, e.g., ATP-dependent remodelers (e.g., SWI/SNF, RSC, NURF, CHRAC, and ACF), other histone modifying enzymes such as histone acetyltransferases (e.g., the GCN5 family of protein complexes, the CBP/p300 family of acetylases, and TAF250), histone deacetylases (e.g., the RPD3 family), histone kinases, histone ubiquitination enzymes, and histone methyltransferases, and the modulators of these chromatin remodeling enzymes.

Other features and advantages of the invention will be apparent from the following detailed description, and from the claims.

BRIEF DESCRIPTION OF THE DRAWINGS

FIG. 1B is a schematic representation of the SalI modified 5S DNA repeat used to prepare the DNA template of FIG. 1a.

FIG. 6 is a graph showing initial rate measurements of restriction enzyme activity in the presence of the SWI/SNF complex. An 8 nM solution of nucleosome array was incubated in the presence of 1 mM ATP with 5000 U/ml SalI for 1 hour. SWI/SNF complex was then added to reach final concentrations of either 2 nM (○), 1 nM (□), 0.5 nM (Δ) or 0.25 nM (▽). As a control, SWI/SNF buffer was added (●). The fraction of cut array was determined for samples taken at 2 minutes ±5 second intervals for 10 minutes and then as indicated.

FIG. 8 is a graph showing DNA accessibility of SWI/SNF remodeled nucleosome arrays. Reactions containing 2 nM array, 100 U/ml SalI, and no ATP (■), 2 nM array, 100 U/ml SalI, and 1 mM ATP (□), or 2 nM array, 5000 U/ml SalI. and no ATP (●), were started by addition of SWI/SNF complex to a final concentration of 4 nM. 5000 U/ml of SalI was added to a reaction lacking ATP (●) to determine the fraction of nucleosome arrays bearing occluded restriction endonuclease sites. The fraction of uncut array ($f_{uncut}$) was determined at the indicated time points after addition of SWI/SNF complex.

FIG. 9 is a graph showing that SWI/SNF functions catalytically to remodel nucleosome arrays. A reaction containing 5000 U/ml SalI, 1 mM ATP, and 2 nM SWI/SNF complex was started by the addition of nucleosome arrays (2 nM). Aliquots were taken for analysis after 5, 15, 45, and 59 minutes. An additional 2 nM of nucleosome arrays was added 3 times at 1 hour intervals (●) and aliquots taken as in the preceding hour. Also shown is a parallel SWI/SNF-SalI coupled reaction (○).

FIG. 10A is a graph showing that SWI/SNF remodeling of nucleosome arrays requires continuous ATP hydrolysis. Chicken erythrocyte histone octamer core nucleosome arrays (4 nM) and SWI/SNF complex (4 nM) were incubated with 1 mM ATP for 1 hour in the presence (□) or absence (■ and ●) of 1 unit of apyrase. At t=60 minutes, 5000 U/ml SalI was added with 1 unit of apyrase (■) or without 1 unit of apyrase (□ and ●).

FIG. 10B is a graph showing the identical experiment as described in FIG. 10A, but in which nucleosome arrays were assembled with HELA cell histone cores.

DETAILED DESCRIPTION

The present invention utilizes nucleosome arrays in assays that couple the activity of a nucleosome remodeling enzyme to restriction endonuclease activity. Each nucleosome array includes a DNA template and multiple histone octamer cores. The DNA template includes a linear chain of multiple repeats of a DNA sequence ("DNA repeats"), preferably in a head-to-tail orientation, each of which functions as a nucleosome positioning sequence. Each of the histone octamer cores is associated with one of the DNA repeats of the DNA template to form individual nucleosomes that collectively form the nucleosome array.

To quantitate nucleosome DNA accessibility, one or more DNA repeats, preferably internal repeats, are provided with one or more unique restriction endonuclease sites. The DNA repeats including the unique restriction site preferably function as nucleosome positioning sequences, and preferably all DNA repeats in the nucleosome array function as nucleosome positioning sequences. In those instances where multiple repeats in a nucleosome array are provided with unique restriction endonuclease sites, each of these repeats of the nucleosome array can have the same or different restriction endonuclease sites.

The nucleosome array is assembled using purified histone cores and purified DNA templates to yield an array of multiple positioned nucleosomes in which one or more of the DNA repeats contain a unique restriction endonuclease site. The rate of cleavage of the nucleosome array after exposure to a chromatin remodeling enzyme or enzyme complex provides a direct measurement of the accessibility of the DNA in the nucleosome array.

Typically, the nucleosome arrays include 5 or more, generally 10 to 12 DNA repeats, and associated nucleosome cores to form a nucleosome array that simulates or mimics chromatin under in vivo conditions. The larger the nucleosome array the more closely it mimics physiological chromatin, thus, even larger nucleosome arrays can be prepared, e.g., based on DNA templates having up to 35, 50, or more DNA repeats.

In addition to more closely simulating in vivo conditions, the ratio of cleavable to uncleavable repeats in the larger (greater than 5 nucleosomes) arrays, i.e., the ratio of repeats bearing the site of the restriction enzyme ("reporter repeats") included in the reaction to those that do not, can be varied to achieve different results. For example, if a remodeling enzyme is being used under conditions where the enzyme is very active, increasing the size of the array, i.e., decreasing the ratio of reporter repeats, to "inert repeats" (i.e., those without a unique restriction site), below 1 to 20, will result in a more sensitive assay. On the other hand, using an array generated with a DNA template bearing more than 1 in 5 reporter repeats will increase the detection level of remodeling events.

The length of the DNA repeats in the template ranges from about 146 base pairs, the minimum number necessary to completely wrap around a nucleosome core, to about 240 base pairs, the exact length depending on the preferred linker lengths of the species under investigation. Longer DNA repeats can also be used so long as the length of the resulting linker DNA is less than the nucleosome binding length of 146 base pairs. However, DNA sequences having more than 240 base pairs are likely to have intervening nucleosome cores bound to the linker regions that may adversely affect the resulting arrays.

Of the total number of DNA repeats in the array, only one or two are typically provided with single or multiple unique endonuclease restriction sites to allow easy quantitation of the cleavage rates. While arrays including multiple DNA repeats in which more than two repeats are provided with restriction sites can be used, quantitation becomes much more difficult. To avoid potential "end effects," e.g., reduced stability and nonphysiological conditions, that also might adversely affect the results, the restriction sites should be provided on DNA repeats associated with internal nucleosome cores, i.e., nucleosome cores having a flanking nucleosome on both sides. Preferably, all of the DNA repeats are of the identical size, although differences in the size of one repeat up to a maximum of 145 additional base pairs can generally be tolerated by the assay system.

Each of the DNA repeats are strong nucleosome positioning sequences that can rotationally and translationally position a nucleosome after in vitro assembly to yield a nucleosome array with a maximum number of occluded restriction endonuclease target sites. Examples of nucleosome positioning sequences include portions of the 5S rRNA gene from *Lytechinus variegatus* (sea urchin) (e.g., as described in Simpson et al., Cell, 42:799–808, 1985), the 5S rRNA gene from *Xenopus borealis* (frog), and the 5S rRNA gene from any other eukaryote, including humans.

Since the 5S rRNA nucleosome positioning sequences operate to position nucleosomes in the same manner in diverse organisms, a compound that modulates the activity of a specific remodeling enzyme in an in vitro assay using a nucleosome array prepared with a DNA template derived from, e.g., the 5S rRNA gene from *Lytechinus variegatus*, should have the same modulating activity in an in vitro assay using a nucleosome array based on a 5S rRNA gene from a different organism, and thus, the same modulating activity in vivo in that different organism as well. In other words, an in vitro assay using a nucleosome array based on the 5S rRNA gene of *Lytechinus variegatus* is reasonably predictive of the activity of a given modulator in many other organisms, including humans.

Other nucleosome positioning sequences, both artificial constructs and naturally occurring sequences, even if less efficient than the 5S rRNA gene in providing a nucleosome array with occluded restriction endonuclease sites, can also be used.

The nucleosome arrays can be constructed using methods well known in the art. Generally, template DNA that contains two or more repeats of a nucleosome positioning sequence can be generated by PCR amplification, restriction digestion of DNA plasmids or other standard molecular biological techniques. For example, individual nucleosome positioning sequences can be generated by PCR amplification of plasmid or genomic DNA containing such sequences and the individual nucleosome positioning sequences concatenated by ligation. To ensure a head-to-tail orientation of DNA repeats, each nucleosome positioning sequence can be provided with restriction endonuclease sites on either end that permit only the desired orientation.

For further manipulation, e.g., the introduction of a modified DNA repeat, i.e., one containing a unique restriction endonuclease site, the DNA template can be introduced into a plasmid by standard techniques. Alternatively, the individual nucleosome positioning sequences can be ligated into existing arrays of distinct nucleosome positioning sequences. Repeats that contain unique restriction sites can be introduced into the nucleosome array at a defined repeat location by standard gene cloning methods, DNA mutagenesis techniques, or by PCR amplification. To allow detection of the restriction digestion products, the template DNA is labelled at one end with a molecular probe (radioactive or non-radioactive).

To assemble the nucleosome array, template DNA (100 μg/ml final concentration) is mixed with purified histone octamers in a high salt buffer (e.g., Tris EDTA (TE)+2 M NaCl) at a molar ratio of histone octamers to DNA repeats to yield the desired occupancy of repeats, typically one mole of octamer per mole of DNA repeat to yield a saturated array. The ionic strength of this mixture is then reduced to <600 mM NaCl by dialysis or dilution, e.g., sequential dialyzation for 1.5 to 6 hours at 4° C. against TE+1M NaCl, TE+0.6 M NaCl, and TE without salt. If necessary, the assembled nucleosome arrays can be purified by glycerol or sucrose gradient centrifugation to remove, e.g., aggregated arrays. Alternatively, the nucleosome arrays can be assembled by other methods well known in the art, e.g., deposition of histone octamers onto DNA using polyglutamate or histone chaperones.

Once obtained, the nucleosome arrays can be used to quantitatively measure nucleosomal DNA accessibility or to screen for modulators, i.e., activators or inhibitors, of chromatin remodeling enzymes or enzyme complexes. To measure nucleosomal DNA accessibility, the nucleosome array is incubated with both the remodeling enzyme and the restriction enzyme. The restriction enzyme mediated DNA cleavage of the arrays is monitored and compared to that of a DNA standard (described below). Reaction parameters such as pH, time, temperature, and reagent concentrations can be optimized according to the requirements of the assay to maximize the combined activity of the remodeling and restriction enzymes.

Generally, the reaction parameters are as follows: pH (7 to 8), time (0.5 to 2 hours), temperature (0 to 37° C.), and reagent concentrations (1000 to 8000 U/ml restriction enzyme and 0.1 to 8 nM chromatin remodeling enzyme or enzyme complex). Optimization of the reaction parameters should take into account (i) the effect of these parameters on the substrate nucleosome array, (ii) the activity of the remodeling enzyme, (iii) the properties of the restriction endonuclease, and (iv) the properties of other reagents included in the reaction (such as the components of the chemical library to be screened) under said conditions.

Preferably, the arrays are first incubated with the restriction endonuclease to eliminate any nucleosome arrays that do not bear occluded restriction endonuclease sites (i.e., sites in DNA associated with a histone core) prior to the addition of the library of putative remodeling enzyme modulators and of the remodeling enzyme itself. The rate of cleavage, which indicates DNA accessibility, is determined by comparison to a standard, such as the rate of cleavage of naked DNA, i.e., DNA not occluded or associated with histone cores to form nucleosomes, or to the rate of cleavage of nucleosome arrays that have not been incubated with the remodeling enzyme.

Any remodeling enzyme or enzyme complex can be analyzed in this manner. Examples include SWI/SNF, histone deacetylases and acetyltransferases, histone methylases/demethylases, histone kinases, histone phosphatase, histone ubiquitinases/deubiquitinases, and as yet unknown histone modifying enzymes, as well as ATP consuming complexes such as RSC, ACF, NURF, CHRAC, and as yet uncharacterized compounds or molecules that increase nucleosomal DNA accessibility to restriction endonucleases either by themselves or by modulating the activity of anyone or more of the above enzymes.

Cleavage can be monitored by electrophoresis and subsequent visualization of the DNA fragments, or by the release into solution of DNA fragments bearing chromophores, or any other easily detectable functional group. The rate of production of such soluble DNA fragments is a direct measure of the rate of cleavage of the DNA which, under conditions where the enzymatic activity of the restriction enzyme exceeds that of the remodeling enzyme, is a direct measure of the remodeling enzymes' activity.

The nucleosome arrays can also be used as screening tools for evaluating potential modulators of nucleosome remodeling enzymes. As a screening tool, the nucleosome array is incubated as described above with a nucleosome remodeling enzyme, a putative modulator of that enzyme, and the restriction endonuclease. Then the rate of the restriction enzyme mediated DNA cleavage is determined as described above and compared against a standard, such as the rate of cleavage in the absence of the putative modulator and/or the rate of cleavage of naked DNA.

In either assay, the reaction conditions can be optimized by modulating pH, temperature, time, ionic strength, monovalent and divalent cation concentrations, as well as by choosing the appropriate nucleosome array as a substrate to ensure maximal possible activity of the nucleosome remodeling enzymes, putative modulators of the remodeling enzymes, and/or the restriction endonuclease. Optimization can generally be performed by first monitoring the effects of these parameters on the restriction enzymes to determine the range of conditions under which the restriction endonuclease function maximally, and then determining under which of these conditions the remodeling enzyme performs best. Conditions that are optimal for both enzymes are then chosen.

High Throughput Screening for Compounds that Modulate Chromatin Remodeling

The nucleosome array systems described herein can also be adapted for automation and high throughput screening for compounds, e.g., small molecules, that modulate, i.e., enhance or inhibit, the activity of chromatin remodeling enzymes. The assembled nucleosome arrays can be immobilized, e.g., on streptavidin-coated microtiter wells by incorporation of a biotinylated nucleotide in the template DNA at one end of the template chain. The other end of the template DNA associated with the nucleosome array could subsequently be modified with a fluorescent nucleotide. In a solution assay, cleavage of the nucleosome array by a restriction enzyme over time could be monitored as a release of fluorescent array into the supernatant of a microtiter well. Because endonuclease digestion is very slow in the absence of a chromatin remodeling enzyme, the background fluorescence would be low over a short period of time, e.g., 0.5 to 2 hours. Addition of a chromatin remodeling enzyme would then provide a measurable signal indicative of DNA accessibility in the nucleosome array. Such immobilized nucleosome arrays would be useful in a high throughput screen to identify small molecules or other compounds that inhibit or enhance this signal.

In general, after assembly of the nucleosome arrays, the arrays can be immobilized on streptavidin-coated microtiter wells as described above via the biotin linkage, each well containing a 20–50 µl reaction volume with 0.1 to 8 nM of immobilized nucleosome array and the appropriate reaction buffer (e.g., 125 mM NaCl, 2.5 mM MgCl, 1 mM DTT, 10 mM Tris-HCl, pH 7.9). A restriction enzyme (2000 to 8000 U/ml) is first added to each microtiter well to a final concentration of 2,000–8,000 units mer ml and the microtiter plate incubated for 0.5 to 2 hours at 0 to 37° C. to cleave nucleosome array templates containing accessible restriction enzyme sites, presumably due to alternative positioning of histone octamers or subsaturation of the array template. Cleaved arrays are removed from the assay by aspirating the supernatant of each reaction mixture and replacing it with fresh reaction buffer.

Next, the chromatin remodeling enzyme (1–4 nM) and then a fresh aliquot of the restriction enzyme are added to the reaction volume in each microtiter well, and the microtiter plates are again incubated at 0 to 37° C. for 0.5 to 2 hours. At intervals sufficient to provide at least four data points, a 5 to 10 µl aliquot of the reaction mixture is removed and the amount of fluorescent label in the aliquot quantitated. To determine the activity of the chromatin remodeling enzyme in the absence of any modulators the difference between the amount of array cleaved per unit of time in the presence and absence of the remodeling enzyme is measured. To screen for inhibitors or enhancers of the chromatin remodeling activity, candidate or putative modulators of the activity of chromatin remodeling enzymes are added to each well of the microtiter plate. The candidate modulator is added at nanomolar to micromolar concentrations, e.g., 0.1 nM to 100 µM, to identify high affinity interactions, and at volumes small enough so as not to alter the buffer conditions. Various concentrations of each candidate modulator can be tested.

Compounds or small molecules identified as enhancers or inhibitors of the chromatin-remodeling, enzyme-dependent cleavage of the nucleosome array are then added to reaction volumes (as previously described) that lacked the remodeling enzyme to screen out compounds that exert their effects on the restriction enzyme, rather than on the remodeling enzyme. Identified compounds or small molecules that inhibit chromatin remodeling are likely to be potent anti-proliferative, anti-fungal, or anti-nuclear receptor (i.e., anti-estrogen) drugs.

Nuclear receptors (e.g., for vitamins A and D, and for steroid hormones), ecdysteroid receptors in invertebrates, prostaglandins, cholesterol metabolism, peptide hormones that signal through Protein Kinase A ("PKA"), and apoptosis all appear to depend on chromatin remodeling to a certain extent for their biological activity. Moreover, different chromatin remodeling complexes are likely to affect only a subset of these different processes. Thus, drugs that target distinct remodelers should be effective modulators of specific nuclear processes. For example, SWI/SNF is required for mammalian steroid receptor function (estrogen and glucocorticoid). Thus, drugs or other small molecules that inhibit SWI/SNF function should eliminate estrogen receptor function and be useful to treat breast cancer.

In addition, chromatin remodeling is emerging as a prerequisite step for virtually every temporally and spatially regulated transcription induction. Specificity can thus be achieved by administration of drugs that affect the ubiquitous process of chromatin remodelling at critical times and/or defined places to affect one particular process.

Applicability of Nucleosome Array Assay To Analysis of Additional Nucleosome Remodeling Enzymes The nucleosome arrays described herein, e.g., the 5S rRNA nucleosome array, possess all of the fundamental properties required to achieve chromosomal level DNA compaction, i.e., 30 nM fibers. Fletcher, T. M. and Hansen, J. C., *Crit. Rev. Eukaryot. Gene Expr.*, 6:149–188 (1996). When such model arrays are incubated in low salt buffers ($\leq$5 mM NaCl), they assume an extended "beads-on-a- string" structure. The addition of monovalent cations alone can induce folding of the arrays to an intermediate level, and addition of divalent cations alone results in structures that are compacted to the same degree as native 30 nM fibers. Importantly, folding of arrays, even in the presence of salts, is absolutely dependent upon the histone N-termini (Schwarz et al., *Biochemistry*, 35:4009–15, 1996) and is sensitive to their acetylation state. Garcia-Ramirez et al., *J. Biol. Chem.*, 270:17923–17928 (1995). The histone N-termini are also required for chromatin folding in vivo (Allan et al., *J. Cell. Biol.*, 93:285–297, 1982), and histone acetylation is correlated with chromatin decondensation and transcription in vivo. Grunstein, M., *TIG*, 6:395–399 (1990). Thus, the biophysical properties of model nucleosome arrays make them ideal substrates for analyzing the properties of chromatin remodeling enzymes other than SWI/SNF, e.g., histone acetyltransferases and deacetylases. Since compaction of nucleosome arrays is predicted to further occlude factor binding sites, the quantitative restriction endonuclease assay described above should prove invaluable for the functional dissection of chromatin or nucleosome remodeling enzymes, and for the screening and development of factors or reagents that influence the biochemical activities of effectors of chromatin remodeling.

The invention will be further described in the following examples, which do not limit the scope of the invention described in the claims.

EXAMPLES

Example 1
DNA Template Construction

A DNA template was prepared as follows. A 2.3 kb DNA fragment encompassing ten *L. variegatus* 5S repeats and five Gal4 binding sites was released from plasmid pG5-208-10 (Owen-Hughes et al., *Science*, 273:513–516 (1996)) by MluI-PvuII digestion. Blunt ends were generated with Klenow polymerase and the DNA fragment was inserted into the SmaI site of a pBS-SK+ (Stratagene) derivative lacking the SpeI site to yield pCL3.

The construct in FIG. 2c of Polach and Widom, *J. Mol. Biol.*, 254:130–149 (1995)(FIG. 1B herein), was amplified by PCR using the following primers:

```
GCGTACCAAGTTAGCATAACTTGAAGGGATTTATA                         (SEQ ID NO:1)

Figure 1A:
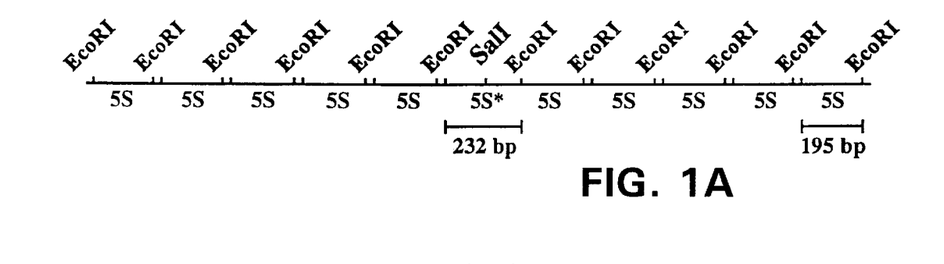
FIG. 1A is a schematic representation of a template DNA used, in combination with histone cores (not shown), to assemble a nucleosome array of eleven nucleosomes, the central one of which bears a single unique restriction endonuclease site. Five head-to-tail 208 base pair 5S rRNA repeats flank both sides of a modified 5S repeat that bears a unique SalI site. Wild type 5S DNA repeats are flanked by EcoRI sites that are 195 base pairs apart, and the SalI modified 5S DNA repeat is located on a 232 base pair EcoRI fragment.
Figure 1B:
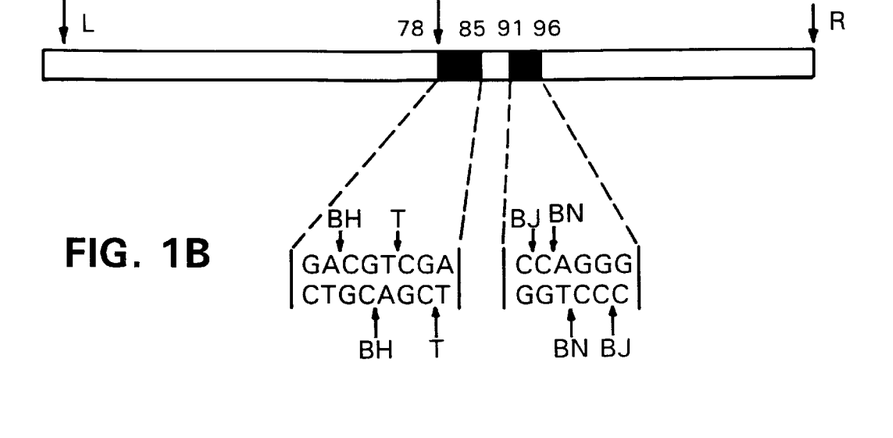

GCGTCTAGTCTAGACCATGGAACCGAGCCCTATGCTTCGCGAGTCCAGTG          (SEQ ID NO:2)
``` and subcloned into the SmaI site of PBS-SK+ to yield plasmid pCL6. The 240 base pair XbaI DNA fragment from pCL6 bearing the modified 5S positioning sequence was inserted into plasmid pCL3 which had been cleaved with NheI and SpeI to release the central 5 Gal4 binding sites and the flanking SalI sites to yield plasmid pCL7c. As shown in FIG. 1A, this DNA template includes five identical DNA repeats on either side of a DNA repeated bearing a SmaI restriction site.

Nucleosome arrays ("SalI arrays") generated (as described in Example 2) using the template DNA from plasmid pCL7c, thus included a DNA template of eleven head-to-tail repeats of the 5S rRNA gene from *Lytechinus variegatus*, each 208 base pairs in length except for the central 5S rRNA repeat (FIG. 1A). This central "reporter" DNA repeat was modified to yield a repeat of 232 base pairs in length containing several unique restriction endonuclease restriction sites, including a single SalI site.

Plasmid pCL7b consists of 9 wild type head-to-tail 208-5S sequences and was obtained in the screen for pCL7c.

Example 2
Preparation of SWI/SNF, Nucleosome Cores, and Nucleosome Arrays

The SWI/SNF complex was purified from 20 liter cultures of yeast strain CY396 as described in Cote et al., *Science*, 265:53–60 (1994), but for the last step wherein the Superose 6 gel filtration step was replaced by sedimentation for 16 hours on a 13–30% glycerol gradient in E buffer (20 mM HEPES (pH 8.0), 350 mM NaCl, 10% glycerol, 0.1% tween 20) at 33,000 g in a SW-28 rotor (Beckman).

Briefly, a whole cell extract was first prepared by lysis of yeast cells with glass beads. The extract was then bound to 20 ml of Ni-NTA agarose in buffer containing 350 mM NaCl. After washing the resin, bound protein was eluted with buffer containing 300 mM imidazole and the eluate was then dialyzed into buffer lacking imidazole, containing 100 mM NaCl. The dialyzed eluate was then loaded onto a native DNA cellulose column and bound protein was eluted with 350 mM NaCl. This eluate was diluted four-fold with buffer lacking salt and then loaded onto a FPLC Mono Q column. The column was washed with a linear salt gradient of 100–500 mM NaCl and SWI/SNF complex eluted at about 350 mM NaCl as detected by western blot analysis of the fractions. SWI/SNF complex was pooled, concentrated with a Centricon microconcentrator, and then sedimented on a 13–30% linear glycerol gradient as described herein.

The concentration of the SWI/SNF complex was determined to be 200 nM by comparative Western blot analysis using an antibody against the SNF5 subunit and seven different concentrations of recombinant SNF5 protein. Quinn et al., *Nature*, 379:844–847 (1996). The approximate concentration of SWI/SNF complex determined by absorbance at 280 nM was in rough agreement with the Western analysis.

Histone octamer cores were purified from chicken erythrocytes (Pel-Freez) as described in Hansen et al., *Biochemistry*, 28:9129–36 (1989). Hela cell histone octamers devoid of histone H1 were prepared as described in Imbalzano et al., *J. Biol. Chem.*, 271:20726–33 (1986). Octamer concentrations were determined by measurements of $A_{230}$. Stein, A., *J. Mol. Biol.*, 130:103–134 (1979).

Large amounts of DNA templates were obtained by a modification of the method described in Hansen, J. C. and Rickett, H., *Anal. Biochem.*, 179:167–170 (1989), except that HhaI, or NotI and HindIII, digestions of 1–2 mg of plasmids pCL7c or pCL7b were followed by FPLC purification on a Biorad 150A exclusion matrix.

Briefly, a HhaI, or a NotI and HindIII, digestion of 1–2 mg of plasmids pCL7c or pCL7b were performed in 1 ml reaction mixtures and at 37° C. for at least 4 hours to ensure complete digestion. Reactions were then fractionated on a Biorad 150A exclusion matrix to separate the template DNA from the smaller restriction fragments derived from the plasmid backbone. Fractions containing purified template DNA were then pooled and concentrated by ethanol precipitation. The templates were labeled by the Klenow polymerase fill-in reaction using $[\alpha^{32}P]dCTP$ (6000 mCi/mmol, Amersham).

Nucleosome arrays were assembled from DNA templates and histone octamer cores in a Spectra/Por microdialyzer (Spectrum, Houston, Tex.), using the salt dialysis protocol of Hansen and Lohr, *J. Biol. Chem.*, 268:5840–5848 (1993), except that 100 mM NaCl was used as the final dialysis step. Apyrase was from Sigma (A-6410) and was diluted to a final concentration of 1 U/ml in 20 mM HEPES (pH 7.9), 1 mM $MgCl_2$, 1 mM DTT, 1 mM EDTA and 1 mg of BSA per ml. When appropriate, SalI restriction enzyme ($10^5$ units/ml) (New England Biolabs) was diluted in the recommended dilution buffer. SDS PAGE analysis of the commercial SalI enzyme stock indicated that 5000 units/ml of SalI is equivalent to a 10 nM solution (data not shown).

Example 3
Characterization of Assembled Nucleosome Arrays

Figure 2:
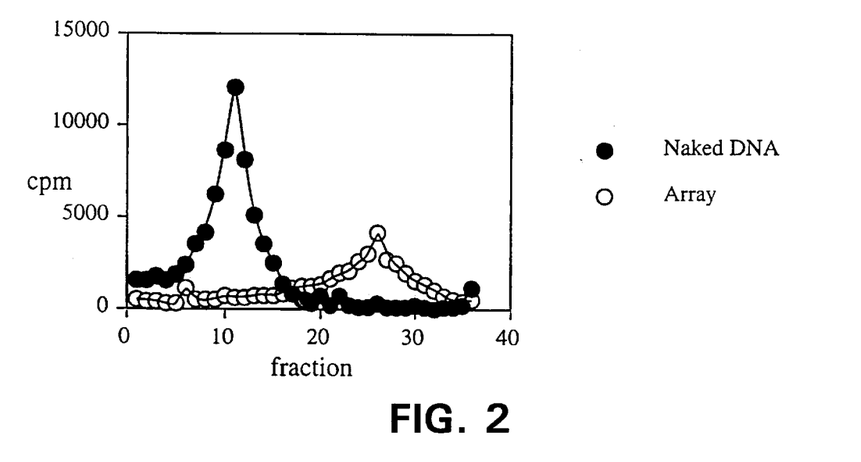
FIG. 2 is a graph showing the glycerol gradient sedimentation of $^{32}$P-labeled naked template DNA (●) or labeled assembled arrays (○). Fractions (0.4 ml) were counted by scintillation and were numbered from the top to the bottom of the gradients.

Four complementary approaches were used to characterize the assembled nucleosome arrays with respect to the efficiency of the assembly, nucleosome positioning, and saturation of the templates with nucleosomes. First, the unassembled and assembled DNAs were sedimented on 13–35% linear glycerol gradients in 10 mM Tris pH 7.5, 125 mM NaCl, 2.5 mM $MgCl_2$, and 1 mM DTT for 16 hours at 33,000 g in a SW-28 rotor (Beckman). The results are shown in FIG. 2 wherein 0.4 ml fractions numbered from the top to bottom of the gradient were counted by scintillation. This analysis indicated that no free DNA template was present after assembly and that the arrays contained an equimolar stoichiometry of the four histone cores.

Second, one end of the template DNA was labeled with $\alpha$-$^{32}$PdATP and the assembled nucleosome arrays digested with micrococcal nuclease in 3 mM $CaCl_2$, 25 mM Tris-Cl (pH 7.4) using 0.01 units of Worthington micrococcal nuclease (Freehold, N.J.) with a nucleosome array concentration of either 4 nM or 40 nM. The micrococcal nuclease digestions yielded identical fragment patterns and showed that the arrays consist of the predicted eleven evenly spaced nucleosomes (data not shown).

Third, the nucleosome arrays were digested with EcoRI restriction endonuclease in an EcoRI saturation assay with an array concentration of 40 nM as described in Hansen et al., *Biochemistry*, 28:9129–9136 (1989), except that the digestions were performed in the SalI digestion buffer as described in Example 4. Gel photographs were scanned and quantitated using NIH Image software. Because each 5S positioning sequence is flanked by two EcoRI sites (FIG. 1A), EcoRI digestion of the nucleosome arrays will release either naked, 195 base pair DNA fragments (or 232 base pairs in the case of the repeat that contains the SalI site), or mononucleosomes which migrate on a native acrylamide gel with an apparent mobility of 400 base pairs.

Using arrays that were assembled at a histone octamer to 5S repeat ratio of 1.0, less than 10% of the 5S repeats migrated as naked DNA, 60% migrated as mononucleosomes, 30% migrated as nucleosome multimers, and less than 2% of the DNA remained in the well of the gel (data not shown). The nucleosome multimers indicate alternative nucleosome positions on the 5S repeats that result in the occlusion of one or more EcoRI sites. The absence of a 232 base pair fragment showed that the SalI site-bearing 5S repeat was efficiently incorporated into a nucleosome. The appearance of 10% free 5S repeats was consistent with the majority of arrays being fully saturated with eleven nucleosomes.

Fourth, an estimate of the level of nucleosome occupancy of the DNA templates was obtained by subjecting assembled nucleosome arrays to a sedimentation velocity analysis in a Beckman XL-A analytical ultracentrifuge equipped with scanner optics as described in Schwarz, P. and Hansen, J. C., *J. Biol. Chem.*, 269:16284–16289 (1994). The $A_{260}$ of the samples used for the sedimentation assays was 0.6 to 0.8. About 80% of the arrays sedimented at 28 to 29S which is consistent with the value expected for a saturated array of eleven nucleosomes. In addition 10% of the arrays appear to sediment as a subsaturated species that may lack one octamer and 10% sedimented as arrays that either contain eleven octamers with a small amount of additional nonspecifically bound histones or as arrays that were slightly folded due to residual salt in the sample.

Upon completion of the assembly of the nucleosome arrays, it was found that the template DNA was arranged into two different organizations. Approximately 50% of the template DNA and histone octamers were organized into the nucleosome arrays described herein. The remainder of the template DNA and histone octamers were organized into structures referred to herein as "pseudo-naked" DNA, structures believed to have an alternate arrangement of the nucleosome cores on the template DNA such that the restriction endonuclease recognition site is more accessible than it is on the correctly assembled nucleosome arrays. To eliminate those arrays that did not contain reporter repeats bearing an occluded restriction site, the nucleosome arrays were incubated with the restriction enzyme prior to addition of the remodeling enzyme. Thus, the activity of the subsequently added chromatin remodeling enzyme or enzyme complex was assessed only on those array templates that remained after this "pre-clearing" step, i.e., the nucleosome arrays bearing occluded restriction endonuclease sites. As a result of the relatively high accessibility of the restriction site, pseudo-naked DNA, like naked DNA, i.e., DNA unassociated with nucleosome cores, has a much higher affinity for restriction enzymes than does nucleosomal DNA.

Example 4
Method of Measuring SWI/SNF-SalI Coupled Enzyme Reactions

For the coupled SWI/SNF-SalI reactions, assembled nucleosome arrays were mixed with SWI/SNF complex purified from yeast cells as described in Example 2 in a buffer containing final concentrations of 125 mM NaCl, 2.5 mM $MgCl_2$, 1 mM DTT, 10 mM Tris-HCl (pH 7.9), 100 mg/ml BSA, and 2.6% glycerol. In those experiments where the continuous hydrolysis of ATP in remodeling was investigated (see Example 10), 1 unit of apyrase was added per 50 ml of reaction mixture. In those experiments where the ATP requirement in remodeling was investigated (see Examples 6–11), ATP was added to a final concentration of 1 mM. The reactions were incubated at 37° C.

At the indicated time points, an aliquot of the reaction was vigorously mixed for 10 seconds with 25 ml water and 50 ml of a 1:1 solution of phenol/chloroform. The purified DNA fragments were resolved by non-denaturing agarose gel electrophoresis in the presence of 50 mg/ml ethidium bromide. The gels were then dried onto 3 MM Whatman® paper. The fraction of uncut array DNA template was obtained by phosphorimager analysis using ImageQuant® software and taking the ratio of uncut signal to the sum of cut and uncut signal present in the lane. Rates of array cleavage were plotted as the fraction of uncut array remaining after various times of incubation with the restriction enzyme and remodeling enzyme.

Example 5
SalI Digestion Conditions and Kinetics

To optimize the nucleosomal DNA accessibility assay on nucleosome arrays remodeled by the SWI/SNF complex, reaction conditions were sought where both the SWI/SNF and the SalI restriction enzyme reactions could take place. The optimal cleavage of naked DNA by SalI requires 150 mM NaCl and 10 mM $MgCl_2$. These cation concentrations, however, are known to favor compaction and self-association of saturated nucleosome arrays. Conditions were therefore sought where SalI would efficiently cleave naked DNA, but where the arrays would be in the extended "beads on a string" conformation. Concomitant titration of $MgCl_2$ and NaCl revealed that SalI had near maximal activity in the presence of 2.5 mM $MgCl_2$ and 125 mM NaCl (data not shown), conditions under which no self-association of the arrays was observed (data not shown). Nucleosome disruption by the SWI/SNF complex, on the other hand, is optimal in 50 to 125 mM NaCl and 3 to 7 mM $MgCl_2$. Thus, all of the experiments reported in this study were conducted in 125 mM NaCl and 2.5 mM $MgCl_2$.

Figure 3:
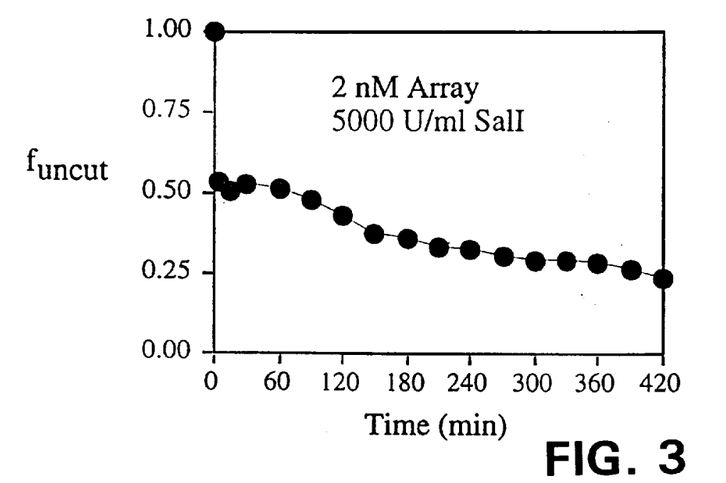
FIG. 3 is a graph showing a time course of SalI digestion of arrays that contain a unique SalI site. Arrays (2 nM) were exposed to 5000 U/ml of SalI. The fraction of uncut nucleosome array DNA is plotted against time.

The digestion kinetics of the new nucleosome arrays are bi-phasic (FIG. 3). In the first phase, 30 to 50% of the template DNA is digested at a rate similar to that of naked DNA, i.e., $2.86 \pm 0.03 \times 10^{-4}$ cleavage events per unit of SalI. This is followed by a second phase where the template DNA is cleaved 300 times more slowly (FIG. 3). Increasing the ratio of octamers to 5S repeats during assembly did not have a large influence on the fraction of template cleaved during the first phase, indicating that the bi-phasic kinetics is not due to subsaturation of the arrays. Furthermore, the bi-phasic kinetics were observed at a higher concentration of array (40 nM) indicating that these kinetics are not due to dilution. In contrast, a large increase in the fraction cleaved in the first phase when sub-saturated arrays were analyzed indicated that the kinetics of the first phase are similar to the kinetics of cleavage of DNA repeats that lack a histone octamer (free repeats). Sub-saturated arrays were generated by lowering the ratio of histone octamers to 5S repeats (data not shown).

To verify that the bi-phasic nature of the cleavage kinetics is not a unique feature of the SalI site-bearing 5S repeat another restriction enzyme, MspI, was used which cleaves each 5S repeat about 20 bp from the predicted dyad axis of the assembled 5S nucleosome. A time course of MspI digestion revealed that each MspI site in the array was also cleaved with bi-phasic kinetics (data not shown). Thus, the bi-phasic nature of the kinetics of restriction enzyme cleavage of 5S repeats after assembly into nucleosome arrays was not a unique feature of the central SalI site-bearing 5S repeat; but rather, is a feature shared by all 5S repeats in the array. By limiting the analysis to the second phase of the restriction enzyme reactions, the first order rate of SalI cleavage per unit of SalI of nucleosomal DNA was determined to be $9.19 \pm 6.4 \times 10^{-7}$ (data not shown). By comparison, the rate of cleavage of the naked DNA template is $2.86 \pm 0.03 \times 10^{-4}$. These values yielded a conformational equilibrium constant of the central nucleosome bearing the SalI site of $3.2 \times 10^{-3}$.

Furthermore, the difference in cleavage rates between naked and array DNA was found to be relatively constant over the range of SalI concentrations used (FIG. 4), suggesting that, in the context of nucleosome arrays, the rate limiting step in restriction enzyme accessibility to nucleosomal DNA is a dynamic equilibrium between the occluded and exposed state of nucleosomal DNA.

Example 6

SWI/SNF Complex Enhancement of Rate of SalI Digestion of Nucleosome Arrays

Figure 5:
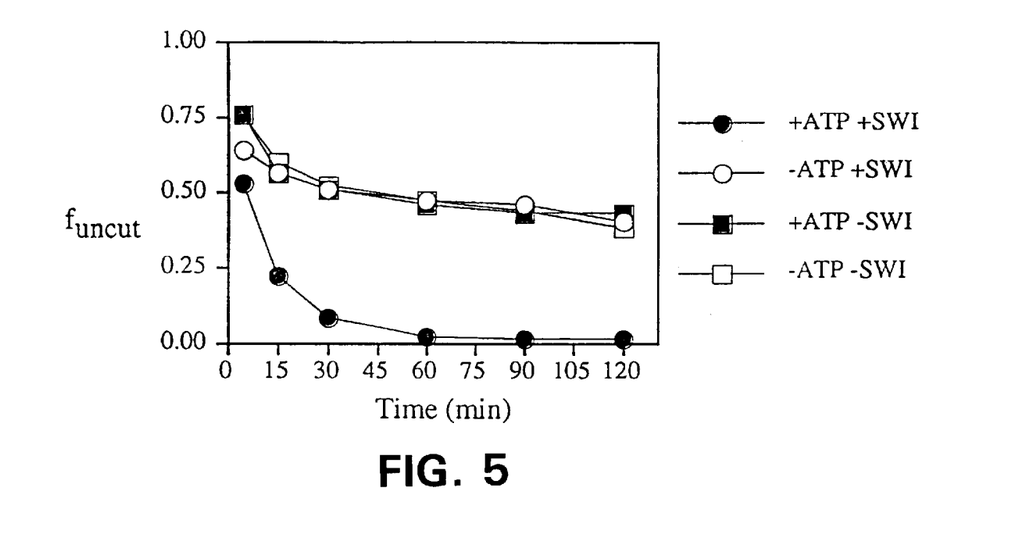
FIG. 5 is a graph showing the quantitation of a time course digestion where 5000 U/ml SalI were mixed with +/−1 mM ATP and +/−4 nM SWI/SNF complex. The reactions were started by addition of 2 nM arrays.

To assess the capacity of SWI/SNF complex to increase the accessibility of the SalI site in the central nucleosome of the nucleosome array, 2 nM of array was exposed to 5000 units/ml of SalI, either in the presence or in the absence of 4 nM SWI/SNF complex and 1 mM ATP (data not shown). The presence of SWI/SNF and ATP did not affect the rate of cleavage of the initial pseudo-naked DNA (data not shown), but cleavage of the array DNA in the second, slow phase, was greatly enhanced (FIG. 5). Under these conditions, SalI digestion of the array DNA was essentially complete after 60 minutes. The enhancement of SalI cleavage required both SWI/SNF and ATP, and ATP could not be substituted with the non hydrolyzable ATP analog, ATPgS (data not shown).

Example 7

Measurement of Initial Reaction Velocity

Figure 6:
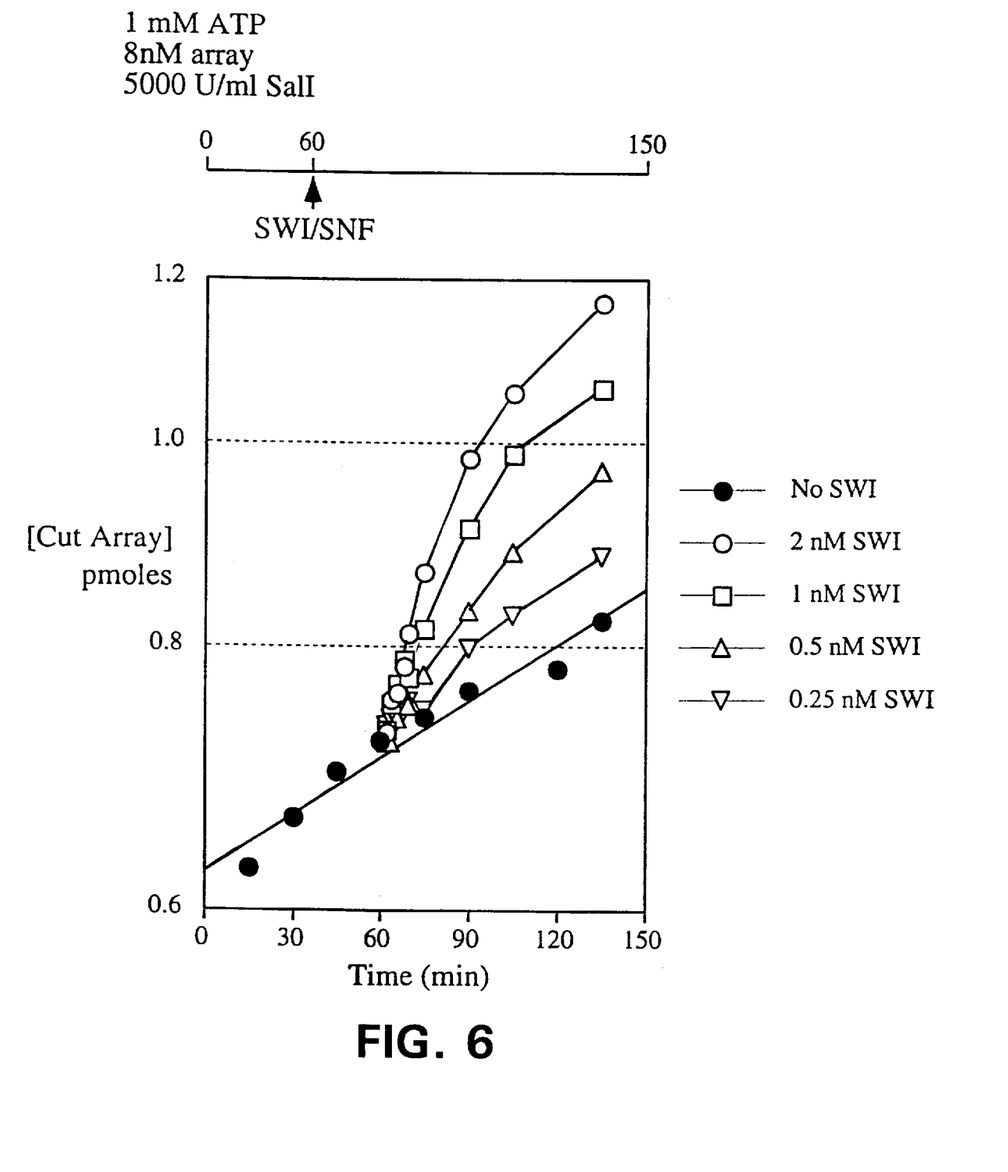
Figure 7:
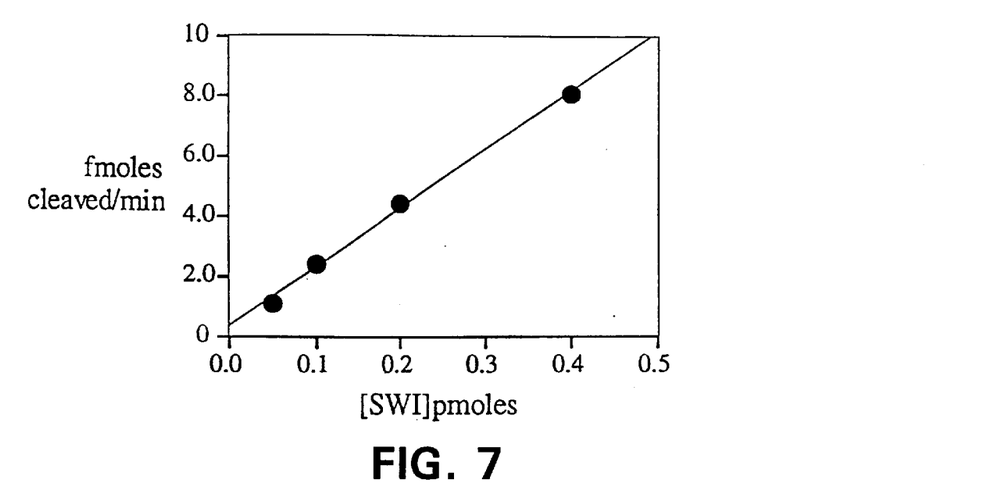
FIG. 7 is a graph plotting the increase in cleavage rates of nucleosome arrays by SalI versus concentration of SWI/SNF. The data were derived from the experiment shown in FIG. 6.

To obtain an apparent rate of SWI/SNF-mediated nucleosome remodeling in the context of the 11-mer array, initial SalI digestion rates were measured under limiting SWI/SNF conditions and with an excess of SalI enzyme. Labeled array (8 nM) was exposed to 5000 U/ml SalI for 1 hour to remove the pseudo-naked DNA from the reaction. After 1 hour, SWI/SNF complex was added to a final concentration of either 2.0, 1.0, 0.5, or 0.25 nM and ATP was added to 1 mM. The extent of SalI cleavage was measured at 2 minute intervals for 10 minutes and longer intervals subsequently (FIG. 6). Initial velocities of SWI/SNF-mediated nucleosome remodeling were obtained by subtracting the SWI/SNF independent cleavage events from the observed cleavage events and are expressed as picomoles of array cleaved per minute (FIG. 6). The initial velocities calculated from the data obtained in the first 10 minutes following SWI/SNF addition were directly proportional to the amount of SWI/SNF added (FIG. 7).

In this SWI/SNF-SalI coupled reaction, 0.2 picomoles of SWI/SNF led to the cleavage of 4 femtomoles of array per minute by SalI. Thus, under conditions where SalI and nucleosomes were in excess, it took one SWI/SNF complex 50 minutes to process one 11-mer array. Assuming that all nucleosomes on the array are equivalent to the central SalI nucleosome, and that SWI/SNF disrupts only one nucleosome of each array per remodeling event, then one SWI/SNF complex remodels one nucleosome every 4.5 minutes ($k_{cat}$= 0.22 $min^{-1}$); a value similar to the turnover numbers obtained for restriction enzymes—4.0 $min^{-1}$, 0.12 $min^{-1}$, and 1.6 $min^{-1}$ for EcoRI (Modrich, P. and Zabel, D., *J. Biol. Chem.*, 251:5866–74 (1976)), SalI (Maxwell, A. and Halford, S. E., *Biochem. J.*, 203:93–8 (1982)), and EcoRV (Halford et al., *Biochemistry*, 27:1771–7 (1988)), respectively.

Example 8

DNA Accessibility in a SWI/SNF Remodeled Nucleosome

To obtain an estimate of the conformational equilibrium constant of a SWI/SNF remodeled nucleosome, conditions were chosen where the rate of SalI cleavage of naked DNA was eight-fold slower than the rate of SWI/SNF-mediated nucleosome remodeling. Under these conditions, the likelihood of SalI encountering an occluded site is very low compared to that of encountering an accessible site. The restriction kinetics therefore reflect the accessibility of only the DNA on the remodeled nucleosomes as restriction endonucleases have a higher binding affinity for naked or pseudo-naked DNA as compared to occluded nucleosomal DNA. Thus, at low concentrations of restriction endonuclease, the affinity of the restriction endonuclease for the occluded sites is too low for cleavage to occur. Thus, the enzyme is only able to recognize the more accessible templates.

Figure 4:
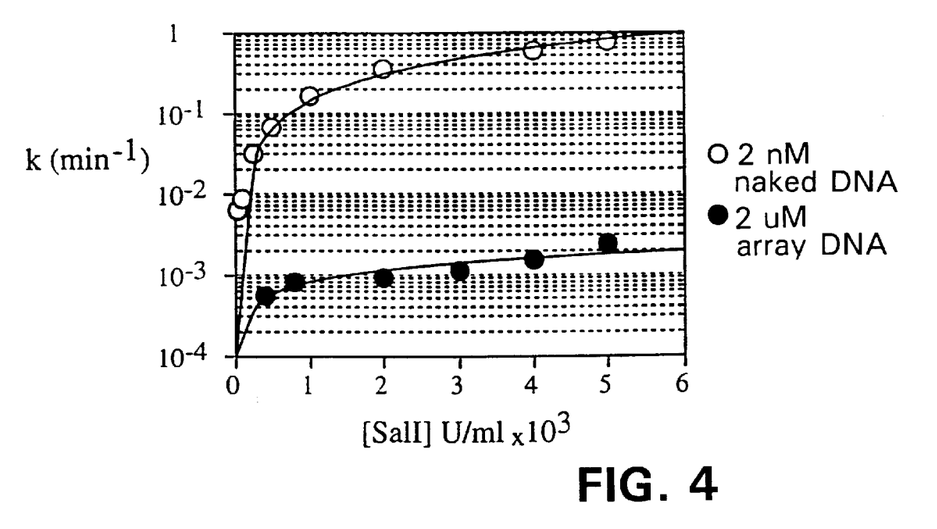
FIG. 4 is a graph showing the dependence of the rate of cleavage of naked DNA (○) or nucleosome array (●) on the concentration of SalI enzyme. Nucleosome arrays (2 nM) were pre-treated with 250 units/ml of SalI for 3 hours before addition of SalI to final concentrations ranging from 400 to 5000 units/ml. Naked DNA (2 nM) was digested with 50 to 5000 U/ml SalI.
Figure 8:
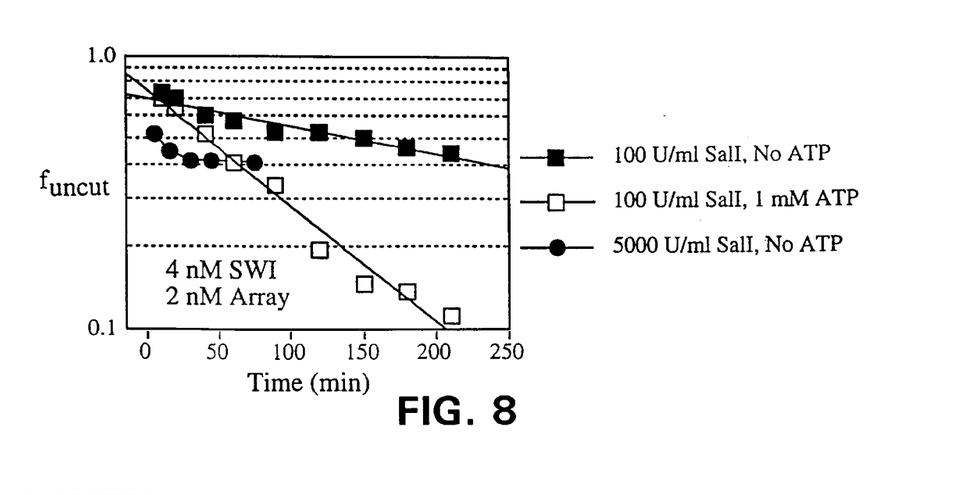

Based on the data provided in FIG. 4 (showing that 100 U/ml of SalI cleaved approximately 10 pmoles of naked template DNA (2 nM) per minute) and FIG. 7 (indicating that a 4 nM solution of SWI/SNF complex could remodel 80 pmoles of assembled array per minute), reactions were established containing +/- ATP, 4 nM SWI/SNF complex, 2 nM array, and 100 U/ml of SalI. In the presence of SWI/SNF, but in the absence of ATP, 55% of the arrays were cleaved after 210 minutes (FIG. 8). At such low SalI concentrations the digestion kinetics are no longer biphasic, suggesting that only the pseudo-naked SalI sites were cleaved in this study (FIG. 8). Consistent with this view, a similar fraction of array template was cleaved at high SalI concentrations very early (FIG. 8). In the presence of SWI/SNF and ATP, cleavage proceeded with first order kinetics, with 89% of the arrays cleaved within 210 minutes (FIG. 8).

Quantitation of the SWI/SNF reaction yielded a first order rate of cleavage per unit of SalI of $9.3\pm4.8\times10^{-5}$ $U^{-1}$ $min^{-1}$ in comparison to a rate of cleavage of naked DNA by SalI of $2.86 +/-0.03\times10^{-4}$ $U^{-1}$ $min^{-1}$ (FIG. 4). Thus, in the presence of SWI/SNF and ATP, the SalI site in the central nucleosome is cleaved only 3-fold slower than naked DNA and about 100 times faster than the un-remodeled nucleosome. Expressed in terms of $K_{conf}$, the remodeled SalI nucleosome has a $K_{conf}$ of $3\times10^{-1}$, two orders of magnitude higher than a control SalI-bearing nucleosome.

Example 9
Multiple Nucleosome Remodeling Events Per SWI/SNF Complex

To determine whether each SWI/SNF complex could remodel more than one nucleosome a classic substrate re-addition experiment was performed. Two nM of SalI nucleosome array (corresponding to 22 nM of nucleosomes) was added to a reaction mixture (described below) three times at 60 minute intervals to a reaction that initially contained 2 nM SWI/SNF complex, 5000 U/ml SalI and 2 nM SalI array. As a control, unlabeled nucleosome arrays were used in the initial incubation and 2 nM of naked labeled DNA was added three times. These control add-ins showed that over 95% of the naked DNA was cleaved within 5 minutes, indicating that SalI activity did not decrease over time (data not shown).

Figure 9:
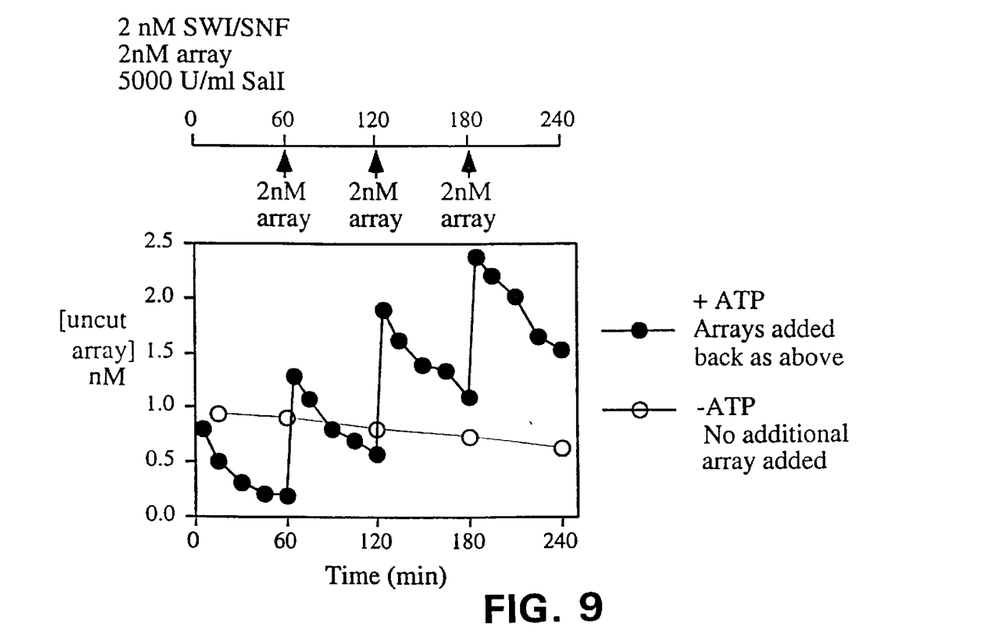

As a second control, ATP was omitted from the reaction, no array was added, and the fraction of uncut arrays was monitored. In this case 47% of the arrays were uncut after 15 minutes and 32% of the arrays were still uncut after 4 hours, indicating that the first order rate of cleavage per unit of SalI of nucleosomal DNA was $3.34\times10^{-7}$ $U^{-1}$ $min^{-1}$ (FIG. 9). In a reaction that contained SWI/SNF, the rate of SalI cleavage of the initial aliquot of the labeled nucleosome array was dramatically enhanced (FIG. 9). Furthermore, after each re-addition of substrate, SWI/SNF was able to stimulate SalI digestion of the nucleosomal DNA. Subtracting the SWI/SNF-independent SalI cleavage of nucleosomal DNA from the SWI/SNF-stimulated SalI cleavage events indicates that 0.5 picomoles of array, corresponding to 5.5 picomoles of nucleosomes, were remodeled by 0.4 picomoles of SWI/SNF complex during the 4 hour timecourse, which demonstrates multiple rounds of nucleosome remodeling events per SWI/SNF complex.

Figures 10A, 10B:
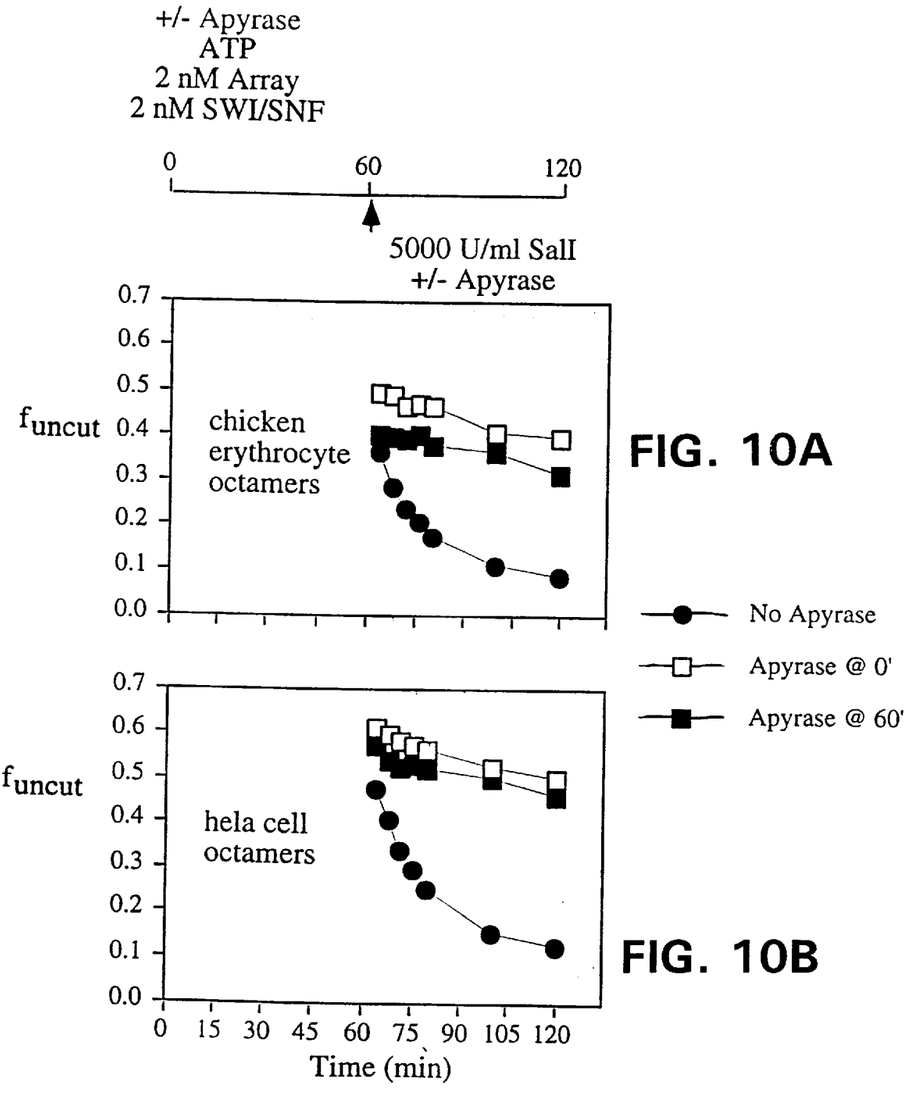

Example 10
SWI/SNF Nucleosome Remodeling is Dependent On Continuous ATP Hydrolysis To test whether the reversibility of SWI/SNF remodeling of nucleosome arrays, apyrase was used to remove ATP at different times during the SWI/SNF-SalI coupled assay. As shown in FIGS. 10A to 10B, 2 nM of nucleosome array, 2 nM SWI/SNF and 1 mM ATP was incubated for 1 hour at 37° C. in the absence of SalI; after which time 5000 U/ml SalI was added. When apyrase was added at the start of the reaction, the rate of SalI cleavage was identical to the rate in the absence of SWI/SNF (□). As shown in FIG. 10A, when apyrase was added concomitantly with SalI (Time 600), the digestion kinetics were identical to the reaction that received apyrase at time zero. At this concentration of apyrase, all detectable ATP is removed in less than two minutes (data not shown). Thus, although nearly 90% of the arrays potentially could have been in the remodeled state after this first 60 minute incubation (FIG. 5 and FIG. 10A), the disrupted state was not stable, and was efficiently reversed before addition of SalI and apyrase. Thus, the chromatin remodeling reaction is rapidly reversible and ATP is continuously required for SWI/SNF-mediated enhancement of SalI cleavage of nucleosomal DNA. This continuous requirement for ATP for nucleosome remodeling was observed with histone octamers from both Hela cells and chicken erythrocytes (FIG. 10B).

Example 11
Non-Targeting of Restriction Endonuclease Bearing Sites of Nucleosome Arrays To determine whether the SalI restriction site preferentially targeted the SWI/SNF complex to the nucleosome bearing the SalI site, competition experiments using unlabelled arrays devoid of SalI sites were performed.

Figure 11:
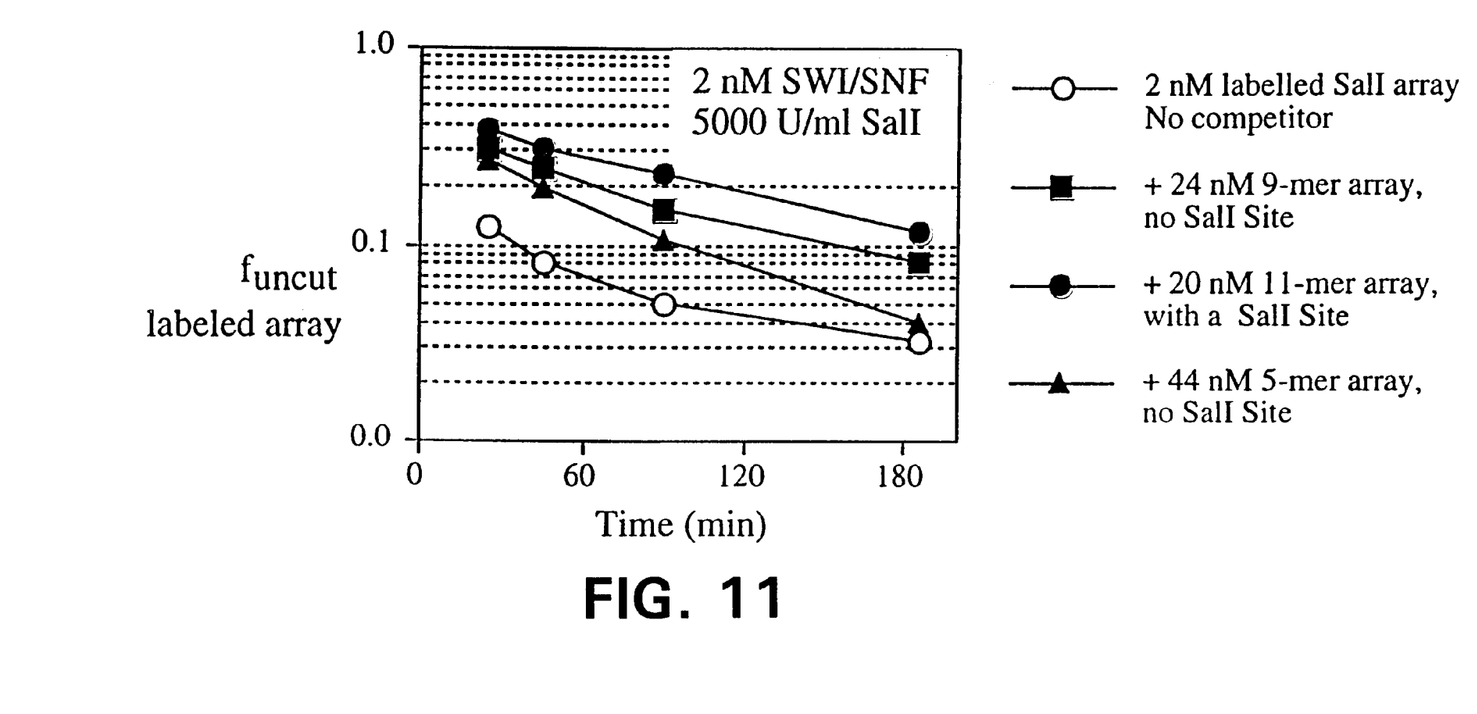
FIG. 11 is a graph showing that SalI does not target SWI/SNF to nucleosomes that contain a SalI site. A reaction containing 2 nM of a labeled nucleosome array (equivalent to 22 nM nucleosomes), 2 nM SWI/SNF complex, and 1 mM ATP was incubated with 5000 U/ml SalI either in the absence (○) or in the presence of a ten-fold excess of competitor nucleosomes located on an identical 11-mer SalI array (20 nM) (●), a 9-mer array (24 nM) that lacks SalI sites (■), or a 5-mer array (44 nM) that lacks SalI sites (▲). The fraction of the uncut, labeled SalI array template was measured after 25, 45, 90 and 186 minutes.

Coupled SWI/SNF-SalI reactions were performed using 2 nM SWI/SNF complex, 5000 U/ml SalI, 1 mM ATP, 2 nM labelled SalI array, and a ten-fold molar excess of nucleosomes incorporated into either (i) an 11-mer (the SalI array), (ii) a 9-mer array lacking a SalI site, or (iii) a 5-mer array (the SalI array template that had been pre-cleaved with SalI prior to assembly). EcoRI digestion followed by native gel electrophoresis indicated that the competitor and labeled arrays were equivalently saturated (>80%, data not shown). The extent of SalI cleavage of the labeled array was measured at 25, 45, 90, and 186 minutes. As can be seen in FIG. 11, the 9-mer array that lacked a SalI site was able to compete for SWI/SNF almost as well as the nucleosomes positioned on the 11-mer array that contained a SalI site. The 5-mer arrays were also able to compete, but were less effective than the larger arrays. Similar results were obtained when competitor arrays were present at only a two-fold molar excess of nucleosomes (data not shown). These results indicate that SalI does not efficiently target SWI/SNF activity, and furthermore that there is a positive correlation between array size and the capacity of arrays to compete for SWI/SNF complex.

Example 12
High Throughput Screening for Molecules that Modulate Chromatin Remodeling Enzymes A DNA array template is labeled at one end with a biotinylated nucleotide and at the opposite end with a fluorescent nucleotide derivative. After nucleosome assembly, arrays are immobilized on streptavidin-coated microtiter wells via a biotin linkage, each well containing a 20–50 $\mu$l reaction volume with 4 nM of immobilized nucleosome array and a reaction buffer (125 mM NaCl, 2.5 mM MgCl, 1 mM DTT, and 10 mM Tris-HCl (pH 7.9)). First, the restriction enzyme SalI is added to each microtiter well to a final concentration of 5000 U/ml. The microtiter plate is then incubated for 1 hour at 37° C. to cleave nucleosome array templates containing accessible SalI restriction enzyme sites, presumably due to alternative positioning of histone octamers or subsaturation of the array template. Cleaved arrays are removed from the assay by aspirating the supernatant of each reaction mixture and replacing it with fresh reaction buffer.

Next, the SWI/SNF chromatin remodeling enzyme (2 nM) and a fresh aliquot of the restriction enzyme SalI is added to the reaction volume in each microtiter well, and the microtiter plates are incubated at 37° C. for 2 hours. At 30 minute intervals a 5 μl aliquot of the reaction mixture is removed and the amount of fluorescent label in the aliquot quantitated by standard techniques. The difference between the amount of array cleaved per unit of time in the presence and absence of the remodeling enzyme represents the activity of the chromatin remodeling enzyme in the absence of any modulators.

To screen for inhibitors or enhancers of the chromatin remodeling activity, candidate or putative modulators of the activity of chromatin remodeling enzymes are added to each well of a microtiter plate after the initial restriction enzyme cleavage reaction to remove nucleosome arrays with accessible restriction enzyme sites. The candidate modulator (100 nM) is added to identify high affinity interactions, and at volumes small enough so as not to alter the buffer conditions. Compounds or small molecules identified as enhancers or inhibitors of the chromatin-remodeling, enzyme-dependent cleavage of the nucleosome array are then added to reaction volumes (as previously described) that lack the remodeling enzyme to screen out compounds that exert their effects on the restriction enzyme, rather than on the remodeling enzyme.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

what is claimed is:

1. A nucleosome array comprising:
   (a) a plurality of DNA sequence repeats linked to form a linear chain of DNA sequence repeats wherein each DNA sequence repeat in the linear chain is a nucleosome positioning sequence; and
   (b) a number of histone octamer cores equal to the number of DNA sequence repeats, wherein each of the histone octamer cores is associated with one of the DNA sequence repeats to form a nucleosome,
   wherein one or two of the DNA sequence repeats comprises a unique endonuclease restriction site that is unique to the nucleosome array and is located internally within a nucleosome positioning sequence.

2. The nucleosome array of claim 1, wherein the number of DNA sequence repeats and nucleosomes is at least 6.

3. The nucleosome array of claim 1, wherein the DNA sequence repeats range in length from about 146 base pairs to about 240 base pairs.

4. The nucleosome array of claim 3, wherein the DNA sequence repeats each have a length of about 208 base pairs.

5. The nucleosome array of claim 1, wherein the DNA sequence repeats are derived from a nucleic acid sequence selected from the group consisting of the 5S rRNA gene of *L. variegatus*, and the 5S rRNA gene of *X. Borealis*.

6. The nucleosome array of claim 5, wherein the DNA sequence repeats are derived from the 5S rRNA gene of *Lytechinus variegatus*.

7. The nucleosome array of claim 1, wherein one of the DNA sequence repeats comprises a single, unique endonuclease restriction site that is unique to the nucleosome array.

8. The nucleosome array of claim 7, wherein the DNA sequence repeat comprising the single, unique endonuclease

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 35 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:1:

GCGTACCAAG TTAGCATAAC TTGAAGGGAT TTATA                                      35

(2) INFORMATION FOR SEQ ID NO:2:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:2:

GCGTCTAGTC TAGACCATGG AACCGAGCCC TATGCTTCGC GAGTCCAGTG                      50 restriction site is positioned between two of the other DNA sequence repeats of the linear chain that lack the unique restriction site.

9. The nucleosome array of claim 1, wherein two of the DNA sequence repeats each comprise a unique endonuclease restriction site that is unique to the nucleosome array.

10. The nucleosome array of claim 9, wherein each of the DNA sequence repeats comprising the unique endonuclease restriction site is positioned between two of the other DNA sequence repeats of the linear chain that lack the unique restriction site.

11. A method for quantitatively measuring the accessibility of nucleosomal DNA, the method comprising
  (a) obtaining a nucleosome array of claim 1;
  (b) incubating the nucleosome array with a restriction endonuclease specific for the unique restriction site; and
  (d) measuring the rate of restriction endonuclease cleavage of the nucleosome array, whereby the rate of cleavage indicates the accessibility of the nucleosomal DNA.

12. A method for quantitating the activity of a chromatin remodeling enzyme, the method comprising
  (a) obtaining a nucleosome array of claim 1;
  (b) incubating the nucleosome array with a chromatin remodeling enzyme;
  (c) incubating the nucleosome array with a restriction endonuclease specific for the unique restriction site; and
  (d) comparing the rate of restriction endonuclease cleavage of the nucleosome array in the presence of the chromatin remodeling enzyme with a standard rate of cleavage in the absence of the chromatin remodeling enzyme, whereby the comparative rate of cleavage indicates the activity of the chromatin remodeling enzyme.

13. A method for determining whether a candidate compound is a modulator of a chromatin remodeling enzyme, the method comprising
  (a) obtaining a nucleosome array of claim 1;
  (b) incubating the nucleosome array with a chromatin remodeling enzyme and the candidate compound to create a nucleosome array mixture;
  (c) incubating the nucleosome array mixture with a restriction endonuclease specific for the unique restriction site; and
  (d) comparing the level of restriction endonuclease cleavage of the nucleosome array mixture with a standard level of cleavage of the nucleosome array in the presence of the chromatin remodeling enzyme without the candidate compound, whereby a change in the level of cleavage indicates the candidate compound is a modulator of the chromatin remodeling enzyme.

14. The method of claim 11, wherein the chromatin remodeling enzyme is selected from the group consisting of the SWI/SNF complex, homologues of the SWI/SNF complex, NURF, CHRAC, ACF, RSC, and histone post-translational modifying enzymes.

15. The method of claim 12, wherein the chromatin remodeling enzyme is selected from the group consisting of the SWI/SNF complex, homologues of the SWI/SNF complex, NURF, CHRAC, ACF, RSC, and histone post-translational modifying enzymes.

16. The method of claim 13, wherein the candidate compound inhibits the activity of the chromatin remodeling enzyme.

17. The method of claim 13, wherein the candidate compound enhances the activity of the chromatin remodeling enzyme.

* * * * *